(12) United States Patent
Kopriva

(10) Patent No.: US 8,224,427 B2
(45) Date of Patent: Jul. 17, 2012

(54) METHOD FOR REAL TIME TUMOUR VISUALISATION AND DEMARCATION BY MEANS OF PHOTODYNAMIC DIAGNOSIS

(75) Inventor: Ivica Kopriva, Zagreb (HR)

(73) Assignee: Ruder Boscovic Institute, Zagreb (HR)

( * ) Notice: Subject to any disclaimer, the term of this patent is extended or adjusted under 35 U.S.C. 154(b) by 358 days.

(21) Appl. No.: 12/597,412

(22) PCT Filed: Apr. 25, 2007

(86) PCT No.: PCT/HR2007/000013
§ 371 (c)(1),
(2), (4) Date: Oct. 23, 2009

(87) PCT Pub. No.: WO2008/132522
PCT Pub. Date: Nov. 6, 2008

(65) Prior Publication Data
US 2010/0130870 A1   May 27, 2010

(51) Int. Cl.
*A61B 6/00* (2006.01)
(52) U.S. Cl. ...................................................... 600/476
(58) Field of Classification Search .................. 600/160, 600/109, 476, 477, 478, 407
See application file for complete search history.

(56) References Cited

U.S. PATENT DOCUMENTS

| 5,706,402 A | 1/1998 | Bell |
| 5,784,162 A | 7/1998 | Cabib et al. |
| 5,845,639 A | 12/1998 | Hockman et al. |
| 5,865,754 A | 2/1999 | Sevick-Muraca et al. |
| 6,161,031 A | 12/2000 | Hockman et al. |
| 6,728,396 B2 | 4/2004 | Wang |

(Continued)

FOREIGN PATENT DOCUMENTS
WO   93/25141   12/1993
(Continued)

OTHER PUBLICATIONS

Hyvarinen et al., Independent Component Analysis, 2001, John Wiley & Sons, Inc.
PCT International Search Report, PCT/HR2007/000013, dated May 15, 2008.
(Continued)

*Primary Examiner* — Brian Casler
*Assistant Examiner* — Amanda Lauritzen
(74) *Attorney, Agent, or Firm* — Nixon Peabody, LLP; Jeffrey L. Costellia

(57) ABSTRACT

Proposed invention is related to the field of photodynamic therapy and photodiagnosis. Specifically, a new algorithm is presented for visualization and spatial demarcation of various types of tumors and unhealthy tissue through unsupervised segmentation of the fluorescent multispectral image. Image is acquired through recording of the emission of the tissue illuminated by the light that induces fluorescence in the tumor. For this purpose tissue is treated by photo sensitizer. Algorithm for real time visualization and spatial demarcation of the tumor by means of the analysis of fluorescent image consists of the recording of the fluorescent image (1) that represents linear combination of the unknown classes S by multispectral camera, transformation of the fluorescent multispectral image into new multispectral image (2) applying nonlinear dimensionality expansion, linear transformation of the multispectral image (2) with extended dimensionality, independent component analysis of the innovation representations of the multispectral image (3) that is result of the transformation of the fluorescent image (1) and multispectral image (2), extraction o the tumor map or class of interest in accordance with the chosen criterion and visualization of tumor on monitor.

9 Claims, 12 Drawing Sheets

U.S. PATENT DOCUMENTS

| | | | |
|---|---|---|---|
| 6,944,571 B2 | 9/2005 | Hahn et al. | |
| 7,341,557 B2 * | 3/2008 | Cline et al. | 600/160 |
| 2005/0280813 A1 | 12/2005 | Jones et al. | |
| 2006/0004292 A1 | 1/2006 | Beylin | |
| 2006/0200318 A1 | 9/2006 | Morishita et al. | |
| 2008/0228037 A1 * | 9/2008 | Cline et al. | 600/160 |
| 2009/0209865 A1 * | 8/2009 | Hasegawa | 600/475 |
| 2009/0318815 A1 * | 12/2009 | Barnes et al. | 600/473 |
| 2010/0049055 A1 * | 2/2010 | Freudenberg et al. | 600/475 |

FOREIGN PATENT DOCUMENTS

| | | |
|---|---|---|
| WO | 96/14795 | 5/1996 |
| WO | 96/17309 | 6/1996 |
| WO | 2005/040739 | 5/2005 |
| WO | 2008132522 | 11/2008 |

OTHER PUBLICATIONS

Andersson-Engels et al., Medical Diagnostic System Based on Simultaneous Multispectral Fluorescence Imaging, Applied Optics, Dec. 1, 1994, pp. 8022-8029, vol. 33, No. 34, OSA, Optical Society of America, Washington, DC, US.

Siegel et al., Whole-field five-dimensional fluorescence microscopy combining lifetime and spectral resolution with optical sectioning, Optics Letters, Sep. 1, 2001, pp. 1338-1340, vol. 26, No. 17.

Du et al., Multispectral image classification using independent component analysis and data dimensionality expansion approaches, Proceedings of SPIE, 2004, pp. 374-381, vol. 5546.

Okimoto et al., New features for detecting cervical pre-cancer using hyperspectral diagnostic imaging, Proceedings of the SPIE, 2001, pp. 67-79, vol. 4255.

* cited by examiner

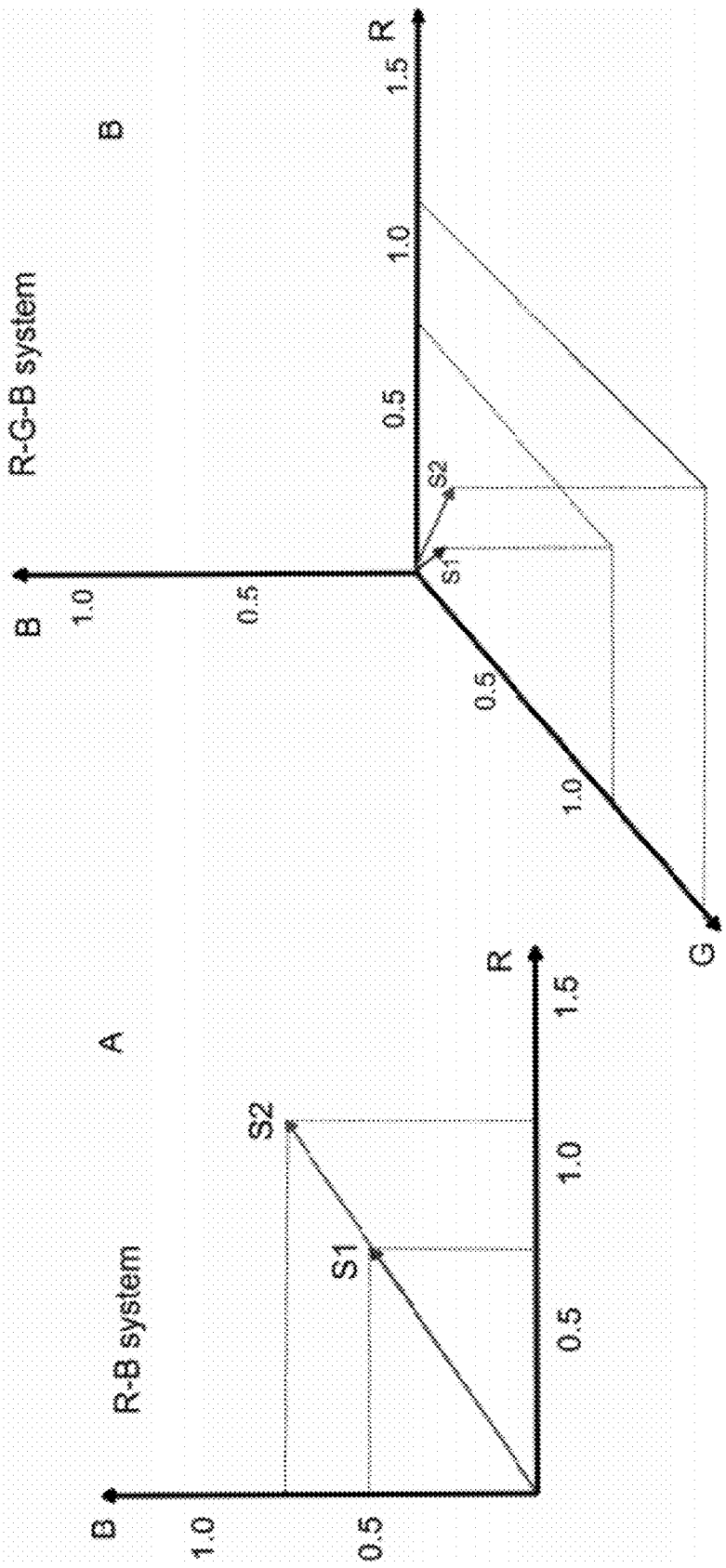

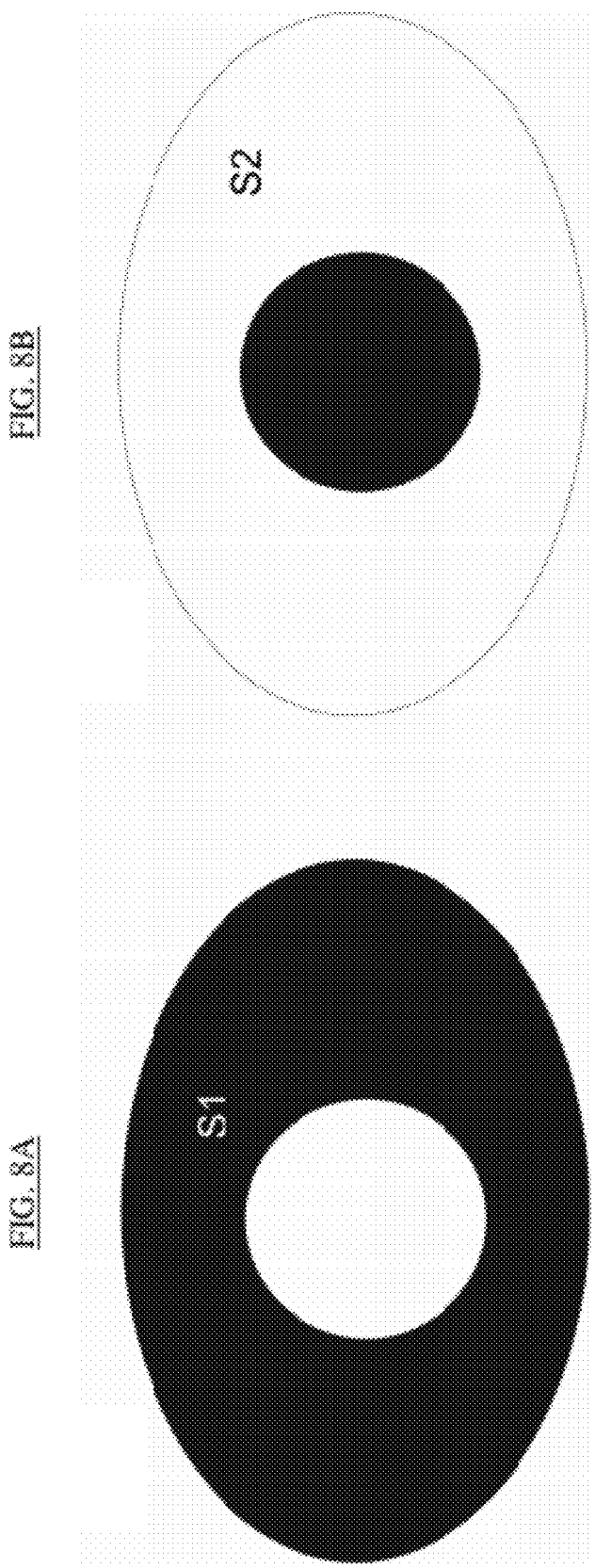

METHOD FOR REAL TIME TUMOUR VISUALISATION AND DEMARCATION BY MEANS OF PHOTODYNAMIC DIAGNOSIS

TECHNICAL FIELD

Proposed invention is related to the field of photodynamic therapy and photodiagnosis. Specifically, the invention is related to the novel method for visualisation and spatial demarcation of the various types of tumours, i.e. unhealthy tissues, by means of unsupervised segmentation of the fluorescent multispectral image. The image is obtained by acquiring emission of the fluorescence of the illuminated tissue. For this purpose the tissue is treated by photo sensitizer. As an example we mention δ-5-aminolaevulinic acid (ALA), with the ability to induce a fluorophore such as protoporphyrin IX (Pp IX) which has a capability of auto-fluorescence when illuminated with the light of a specific wavelength. More detailed description of the photo sensitizers used to induce fluorophores in the tumour tissue is given in the proceeding state-of-the-art section.

STATE OF THE ART

Existing systems for visualisation and demarcation of tumours are based on visualisation of fluorophores accumulated in the tumour tissue by means of the system for the acquisition of the fluorescent image. Fluorescent image can be obtained in various ways depending on the properties of the chosen fluorophore. The basis for the successful visualisation of the tumour is an increased concentration of the fluorophore in the tumour tissue that is achieved after few hours of the treatment by photo sensitizer.

Example that is often used for the photo sensitizer is δ-5-aminolaevulinic acid (ALA). It induces Pp IX which has ability of selective fluorescence in the wavelength interval between 600 nm and 700 nm after being illuminated by 405 nm. (Koenig F, Knittel J, Stepp H. Diagnostic Cancer in Vivo. Science 2001; 292: 1401-1403; Bäumler W, Abels C, Szeimies R M. Fluorescence Diagnosis and Photodynamic Therapy. Dermatology. Med. Laser Appl. 2003; 18:47-56.). As an example, by using this fluorophore and device schematically shown in FIG. 1, that consists of the light illuminator, CCD camera and computer, it is possible to visualise various types of the skin tumours.

For the purpose of the visualisation of the tumour on the cell level nano-particles are used as fluorescent markers. An example is green fluorescent protein with the ability to label tumour cells through the mechanism of selective bonding. (Hasegawa S, Yang N, Chishima T, Miyagi Y, Shimada H, Moossa A. R., Hoffman M. R. In vivo tumor delivery of the green fluorescent protein gene to report future occurrence of metastasis. Cancer Gene Therapy 2000; 10: 1336-1340; R. M. Hoffman. Green fluorescent protein imaging of tumor growth, metastasis, and angiogenesis in mouse models. The Lancet Oncology 2002; 3: 546-556.)

By combining such cell markers and device schematically shown in FIG. 2, that consists of endoscope, fluorescent microscope, CCD camera and computer, it is possible to visualise a tumours of the lung, prostate, stomach, liver, brain, lymph nodes, bone, pancreas, colon, etc.

For the purpose of the visualisation of the brain tumour nano-particle CLIO-Cy5.5 is used as a fluorescent marker. Simultaneously, it is used as a contrast agent for magnetic resonance imaging and fluorescent agent for near infrared imaging. This agent enables recording of the multimodal image of the brain through combination of the magnetic resonance image and near infrared fluorescent image. Application of the nano-particle CLIO-Cy5.5 in visualisation of the brain tumours is described in: Train R, Figueiredo J. L., Pittet M. J., Weissleder R., Josephson L, Mahmood U. Fluorescent Nano-particle Uptake for Brain Tumor Visualization. Neoplasia 2006; 4: 302-311.

Multimodal imaging is also used for the purpose of the visualisation of the surface tumours on small animals. An example includes combination of the fluorescent optical image and radio image recorded by gamma camera. Hematoporphyrin is used as photo sensitizer to generate fluorescent optical image while radio-marker Tc-99m is used to generate radio image. Such system is described in: Autiero M., Celentano L, Cozzolino R, Marotta M, Mettivier G, Montesi M. C., Riccio P, Roberti G, Russo P. Experimental Study on In Vivo Optical and Radionuclide Imaging in Small Animals. IEEE Transactions on Nuclear Science 2005; 52: 205-209; Celentano L, Laccetti P, Liuzzi R, Mettivier G, Montesi M. C., Autiero M., Riccio P, Roberti G, Russo P. Preliminary Tests of a Prototype System for Optical and Radionuclide Imaging in Small Animals. IEEE Transactions on Nuclear Science 2003; 50: 1693-1701.

One of the methods used to calculate tumour demarcation line by visualisation of the Pp IX is the ratio imaging method: Scott M A, Hopper C, Sahota A, Springett R, Mcllroy B W, Bown S G, MacRobert A J. Fluorescence Photodiagnostics and Photobleaching Studies of Cancerous Lesions using Ratio Imaging and Spectroscopic Techniques. Lasers Med Sci 2000; 15:63-72. The method calculates ratio between intensity of the red component of the RGB image (600 to 700 nm) and intensity of the green component of the RGB image (450 to 550 nm). Thus, visual contrast between tumour and healthy tissue is greatly enhanced. Let the image obtained by this method be denoted as: RG=R/G. Dynamic ratio of the RG image is large due to the fact that division operation involves division with very small numbers. In order to preserve contrast of the RG image a threshold is introduced. Intensities of all the pixels in RG image with a value greater than a threshold value are made equal to the threshold value. This is a serious disadvantage of the ratio imaging method because the optimal threshold value is highly dependent on the intensity of the fluorescence. Because of that, the ratio imaging method is highly sensitive on the variation of the fluorescence intensity level. A various reasons can lead to this variation: variability of the time interval of the tumour administration by means of photo sensitizer, variability of the intensity of illuminating light, as well as variability of the sensitivity of the image acquisition system. Described sensitivity can significantly influence accuracy of the tumour demarcation by means of the ratio imaging method. As it will be described one of the important features of the proposed invention is robustness with respect to the variation of the intensity level of the fluorescent image.

Yet another method for the spatial demarcation of the tumour by visualisation of Pp IX is the optimal threshold method: Ericson M B, Sandberg C, Gudmundson F, Rosén A, Larkö O, Wennberg A M. Fluorescence contrast and threshold limit: implications for photodynamic diagnosis of basal cell carcinoma in Journal of Photochemistry and Photobiology B: Biology 2003; 69: 121-127. This method classifies as a tumour areas of the fluorescent image with the intensity level greater than the value set by the threshold. The threshold is defined as a value of the average intensity level corrected by an appropriate factor. It has been empirically found that the correction factor varies between 1.4 and 1.6 if the treatment of the tumour with ALA is between three and four hours. Such imprecision in setting the threshold influences significantly the accuracy of the spatial demarcation of the tumour by means of the optimal threshold method.

Yet another technique frequently used for tumour demarcation is based on the calculation of the difference image obtained by subtracting two or more images recorded in response to the various illuminations. Quite often difference image is superimposed on the image obtained as response on the illumination by white (polychromatic) light. For example in: Fischer F, Dickson E F, Pottier R H, Wieland H. An Affordable, Portable Fluorescence Imaging Device for Skin Lesion Detection Using a Dual Wavelength Approach for Image Contrast Enhancement and Aminolaevulinic Acid-induced Protoporphyrin IX. Part. I. Design, Spectral and Spatial Characteristics. Lasers Med Sci 2001; 16:199-206, a procedure has been described that superimposes difference image, obtained by illuminations with two monochromatic lights, on an image obtained by illumination with polychromatic light. In principle, this type of methods has an increased sensitivity against the variability of the image intensity level what has significant influence on the accuracy of the demarcation. In order to produce spatial tumour map with good visual contrast the image difference methods require high intensity level of the illuminating light. Method proposed in the invention has two advantages in relation to the image difference methods: only one illumination is required; accuracy of the demarcation is significantly increased due to the fact that the method is approximately invariant in relation to the variability of the intensity level of the acquired fluorescent image. Thus, the proposed invention enables estimation of the accurate spatial map of the tumour even when the intensity level of the illuminating light is reduced.

System for the real time acquisition of the image of the brain tumour is described in the U.S. Pat. No. 6,161,031 (B2). System combines frame difference and frame averaging methods with the super-positions on the standard image of the tumour. The goal is to enable a neuro-surgeon to obtain accurate tumour demarcation during the surgery. Regarding accuracy of this image acquisition methods and advantages of the method proposed in the invention, the same comments apply as in the preceding paragraph.

Image difference method is also used in the U.S. Pat. No. 5,845,639 (B2), where a procedure for tumour localisation is based on measuring the oxygen level in the blood. Tissue is illuminated by electromagnetic radiation in visible or infrared part of the spectrum. Spatial map of the tumour is obtained by subtracting reference image (acquired without illumination) from the image obtained as response to illumination. Regarding accuracy of this image acquisition methods and advantages of the method proposed in the invention, the same comments apply as in the preceding paragraphs.

Similarly as in [0009], [0010] and [0011] in the patent application US2006004292 (A1) a real time tumour demarcation method is described. The method is based on the difference between images acquired under illumination with polychromatic and monochromatic light and superimposing difference image onto polychromatic image. Regarding the accuracy of this image acquisition methods and advantages of the method proposed in the invention, the same comments applied as in the preceding paragraphs.

In the document WO 96/14795 yet another system is protected that detects solid tumours in real time, including possibility of gradation and characterization of the tumour tissue. The system includes image processing method that combines frame difference and frame averaging methods by superposition of the difference image on the standard image of the tumour. The same comments apply as for the method described in the preceding paragraphs. Frame difference and frame averaging methods work well if the contrast agent, i.e. photo sensitizer, is used in an appropriate concentration, in the appropriately long time interval and if the intensity of the illuminating light is high enough. The method proposed in this invention has the property to generate spatial map of the tumour with a good visual contrast when the intensity level of the fluorescent image is fluctuating.

In the document WO 93/25141 yet another system is protected that calculates demarcation line and dimensions of the solid tumour tissue in the region of interest. The region of interest is illuminated by the light with high intensity and wavelength that is absorbed by the fluorophore accumulated in the increased concentration in the tumour tissue. The image processing is still based on the averaging of the control image used to form a difference image. In order to increase a visual contrast of the spatial map of the tumour this method additionally assumes illumination with at least two wavelengths. As already commented, the image processing algorithms are quite primitive and based on frame difference and frame averaging. Therefore, it is required that intensity of the illuminating light be high enough, that photo sensitizer be applied with the appropriate concentration and during the time interval that is long enough. Method proposed in the invention has the property to ensure the spatial map of the tumour with a visual contrast the quality of which is in principle not critically dependent on the level of intensity of illuminating light, as well as on the level of the concentration and duration of treatment by the photo sensitizer. In addition to that, the proposed method assumes the tissue illumination in the region of interest by only one wavelength. This significantly simplifies realisation of the photodynamic and photodiagnoses system (instead of two only one laser is used to illuminate the tissue).

In the patent application US20050280813 a method is described that enhances the visual contrast on the image during tumour detection i.e. cytological examinations. The method superimposes images of the tissue in visible and infrared parts of the spectrum, where the fact is used that infrared light is significantly more sensitive on molecular and biochemical variations what represents the basis for tumour detection. Method proposed in the invention requires significantly simplified realisation of the system for photo-dynamic therapy due to the fact that for the purpose of the analysis only image in the visible part of the spectrum has to be used.

In the U.S. Pat. No. 5,865,754 (B2) an optical system is described that is used for non-invasive tumour detection by combining tissue illumination with modulated light and acquisition of the fluorescent image as a response on the illumination. Spatial map of the fluorescence is obtained as a solution of the diffusion equation in the frequency domain. The method proposed in the invention is similar to this method only through the fact that induced fluorescence is used as a basis for the image processing that yields a spatial map of the tumour. The difference is twofold: proposed method does not require illumination with the modulating light and because of that the system for photodynamic therapy is simpler for realisation; the image processing method used to obtain a spatial map of the tumour is geometric-statistical in nature and enables generation of the spatial map of the tumour as a solution of the problem of unsupervised segmentation of the fluorescent multispectral image.

In the U.S. Pat. No. 5,784,162 (B2) a system for localisation of the biological structures, including the skin tumours, is described. It combines spectroscopy, CCD imaging system and algorithms for the multispectral image analysis. For the purpose of the image segmentation an algorithm is used that is based on the similarity principle. This algorithm assumes that it is possible to localize a pixel that contains the pure class i.e. tumour. The remaining pixels are then classified based on similarity with a reference pixel, where the criterion for similarity is an angle between the two spectral vectors. This algorithm belongs to the class of supervised classification methods and is already in use for classification of airborne and spaceborne multispectral and hyperspectral images. The algorithm is characterized by significant errors in classification of spectrally similar classes, especially when the spectral resolution is poor. Such case can be expected in the early stage of tumour development when recorded by a multispectral camera. Then, spectral characteristic of the tumour is similar to the spectral characteristic of the surrounding healthy tissue. Method proposed in the invention is robust in relation to such conditions.

In the patent application US20060200318 (A1) a method is described that is based on the independent component analysis. It is used to separate reflections of the illuminating radiation from the fluorescence in the systems with multiple fluorescence, where the fluorescence from one illumination is superimposed on the reflection from another illumination. By method proposed in the invention that combines nonlinear dimensionality expansion, innovations representation and independent component analysis, it is possible in principle to enhance the level of suppression of the reflected illuminating radiation, because it is spectrally similar (statistically dependent) with a fluorescence.

Tumour demarcation can also be achieved by using methods for supervised and unsupervised segmentation of the fluorescent multispectral image.

Methods for supervised segmentation classify multispectral image in relation to the reference spectral response of the tumour. Accuracy of this approach is significantly limited by the variability of spectral responses of the tumour and healthy tissue. This is especially the case when the spectral resolution is poor, what is the case with an RGB image. One method for supervised segmentation is spectral similarity method already discussed in the preceding paragraphs.

Unsupervised segmentation methods classify multispectral image through looking for extremes of the functional that is a measure of the some of the features for which it is known to represent a class of interest. One of the most successful methods in this domain is independent component analysis (ICA). ICA methods belong to group of statistical methods for unsupervised or blind solution of linear and nonlinear inverse problems. Unsupervised segmentation of the multispectral image belongs to this group of problems. Application of the ICA methods to the problem of unsupervised segmentation of the hyperspectral image is for example described in: Q. Du, I. Kopriva, H. Szu. Independent Component Analysis for Hyperspectral Remote Sensing. Optical Engineering; vol. 45: 017008-1-13, 2006; and also in the U.S. Pat. No. 6,944,571 (B2).

Assumptions upon which the ICA algorithms are built are that unknown classes are statistically independent and non-Gaussian, as well as that the number of linearly independent columns of the unknown basis matrix is greater or equal to the number of classes. One of the most known ICA algorithms is described in the U.S. Pat. No. 5,706,402 (B2), patent application WO 9617309 (A), as well as in the paper: A. J. Bell and T. J. Sejnowski. An information-maximization approach to blind separation and blind deconvolution. Neural Computation; vol. 7, pp. 1129-1159, 1995. Reference literature for the field of blind source separation and independent component analysis is: A. Hyvärinen, J. Karhunen, E. Oja. *Independent Component Analysis*, John Wiley, 2001; A. Cichocki, S. Amari. *Adaptive Blind Signal and Image Processing*, John Wiley, 2002. Advantage of the ICA algorithms in relation to the state-of-the-art methods for tumour demarcation described in the preceding paragraphs, is in their invariance with respect to the variability of the intensity level of the image. This is a consequence of the fact that statistical independence is invariant with respect to the amplitude of the stochastic process.

Statistical independence assumption is however not correct for spectrally similar classes. This is especially the case with the low-dimensional multispectral image with the poor spectral resolution, such as RGB image. Another consequence of the spectrally similar classes is that the unknown basis matrix is badly conditioned i.e. the columns of the basis matrix associated with the spectrally similar classes are linearly dependent. Because of that direct application of the ICA algorithms to unsupervised segmentation of the multispectral image produces inaccurate tumour demarcation.

Problem of blind separation of statistically dependent classes is quite often in biomedical field, as for example in the analysis of the EEG signals and analysis of gene microarrays. Because of that in the U.S. Pat. No. 6,728,396 (B2) an algorithm is protected for blind separation of statistically dependent signals that can even be Gaussian. The basis of the algorithm is identification of the set of measurements where source signals are statistically independent. The unknown basis matrix is then identified by some of the standard ICA algorithms (the FastICA algorithm has been used in the patent) on the set of selected measurements. Criterion used to identify the set of measurements with statistically independent signals is of the ad hoc type and specific for the gene sequence analysis in molecular biology. That is a field where the algorithm is applied. In addition to the fact that identification of the set of measurements with statistically independent processes reduces the effective number of measurements, what influences the accuracy of the ICA algorithms, another disadvantage of this patented algorithm is that its application is limited to the gene sequence analysis.

In references: A. Cichocki, P. Georgiev. Blind source separation algorithms with matrix constraints. IEICE Transactions on Fundamentals of Electronics, Communications and Computer Sciences; E86-A, 522-531, 2003; A. Cichocki. General Component Analysis and Blind Source Separation Methods for Analyzing Multichannel Brain Signals; Statistical and Process Models of Cognitive Aging, Notre Dame Series on Quantitative Methods, Editors: M. J Wenger and C. Schuster. Mahwah, N.J.: Erlbaum, 2007; T. Tanaka, A. Cichocki. Subband decomposition independent component analysis and new performance criteria. Proc. IEEE Int. Conf. on Acoustics, Speech and Signal Processing (ICASSP 2004), Montreal, Canada, 2004, pp. 541-544; some of the algorithms for blind separation of statistically dependent signals are described. These algorithms differ by accuracy and computational complexity but have in common that in a case of statistically dependent processes produce more accurate results than those obtained by direct application of the ICA algorithms. We mention again that unsupervised segmentation of the multispectral image belongs to the class of problems with statistically dependent signals.

Main characteristic of the algorithms for blind separation of statistically dependent signals is that the original data set is transformed in the new data set where transformed unknown classes are less statistically dependent. The condition that has to be fulfilled is that the unknown basis matrix in the linear mixture model has to be invariant with respect to the transform. This enables more accurate estimation of the basis matrix by application of the ICA algorithms on a transformed data. On this way the scale invariance is preserved i.e. the segmentation method preserves robustness with respect to the variability of the intensity level of the fluorescent image. This represents the basis for the robustness of the tumour demarcation method in relation to the variability in duration of the treatment by photo sensitizer as well as in relation to the variability of the intensity of illuminating light.

When segmenting low-dimensional multispectral image, in addition to have statistically dependent classes, there is a problem of spectral similarity between the classes. For example, this is the case in the early phase of the tumour development or when the intensity level of the fluorescence is low. Consequence of the spectral similarity is that corresponding column vectors of the basis matrix, that represent spectral responses of the classes, become linearly dependent. Nonlinear transformation of the multispectral image produces new image with increased dimensionality. Increased dimensionality is a result of the new nonlinearly generated spectral measurement that are mutually linearly independent. Thus, consequence of the increased dimensionality is that classes in transformed image are spectrally less similar i.e. corresponding column vectors in the unknown basis matrix are more linearly independent. Application of this method to the problem of unsupervised segmentation of low-dimensional remotely sensed multispectral image is described in: H. Ren, C. I. Chang. A Generalized Orthogonal Subspace Projection Approach to Unsupervised Multispectral Image Classification. IEEE Transactions on Geoscience and Remote Sensing; vol. 38, No. 6, November 2000, pp. 2515-2528; Q. Du, I. Kopriva, H. Szu. Independent Component Analysis for Classifying Multispectral Images with Dimensionality Limitation. International Journal of Information Acquisition; Vol. 1, No. 3, 2004, pp. 201-215.

Generalization of the nonlinear dimensionality expansion technique described in the preceding paragraph, are the ICA algorithms in the so called kernelised version. First formulation of the kernel ICA method has been given in: Francis R. Bach, Michael I. Jordan. Kernel Independent Component Analysis, Journal of Machine Learning Research, 3, 1-48, 2002. Most important characteristic of this approach is that ICA algorithms are applied on nonlinearly transformed multispectral image in a new high-dimensional space. In principle, this enables more accurate segmentation of the spectrally similar classes.

DETAILED DESCRIPTION OF THE INVENTION

Proposed invention is related to the field of photodynamic therapy and photodiagnosis. More specific, the invention is related to the new method for visualisation and demarcation of the various types of tumours and unhealthy tissue by means of unsupervised segmentation of the fluorescent multispectral image. The case of under-surface tumours is related to the tumours of lung, prostate, stomach, liver, brain, lymph nodes, spine, etc. They are visualised on the cell level by means of green fluorescent protein gene that is used as a fluorescent marker and has ability to bond selectively on tumour cells. When visualising under-surface tumours it is assumed that visualisation device consists of endoscope, fluorescent microscope and multispectral camera. When the intensity level of the fluorescent image is varying especially good visual contrast of the spatial map of the surface tumours is obtained by combined use of the method of nonlinear dimensionality expansion of the multispectral image 1, linear transformation of the multispectral image 2 into innovations representation 3, and applying independent component analysis on the innovations representation 3.

The invention is related to the real time visualisation and demarcation of tumours by unsupervised segmentation of the fluorescent multispectral image 1 by means of the algorithms for nonlinear dimensionality expansion and algorithms for blind separation of statistically dependent processes.

BRIEF DESCRIPTION OF DRAWINGS

In the sequel a more detailed description of the invention will be given with references to the following figures.

Figure 1:
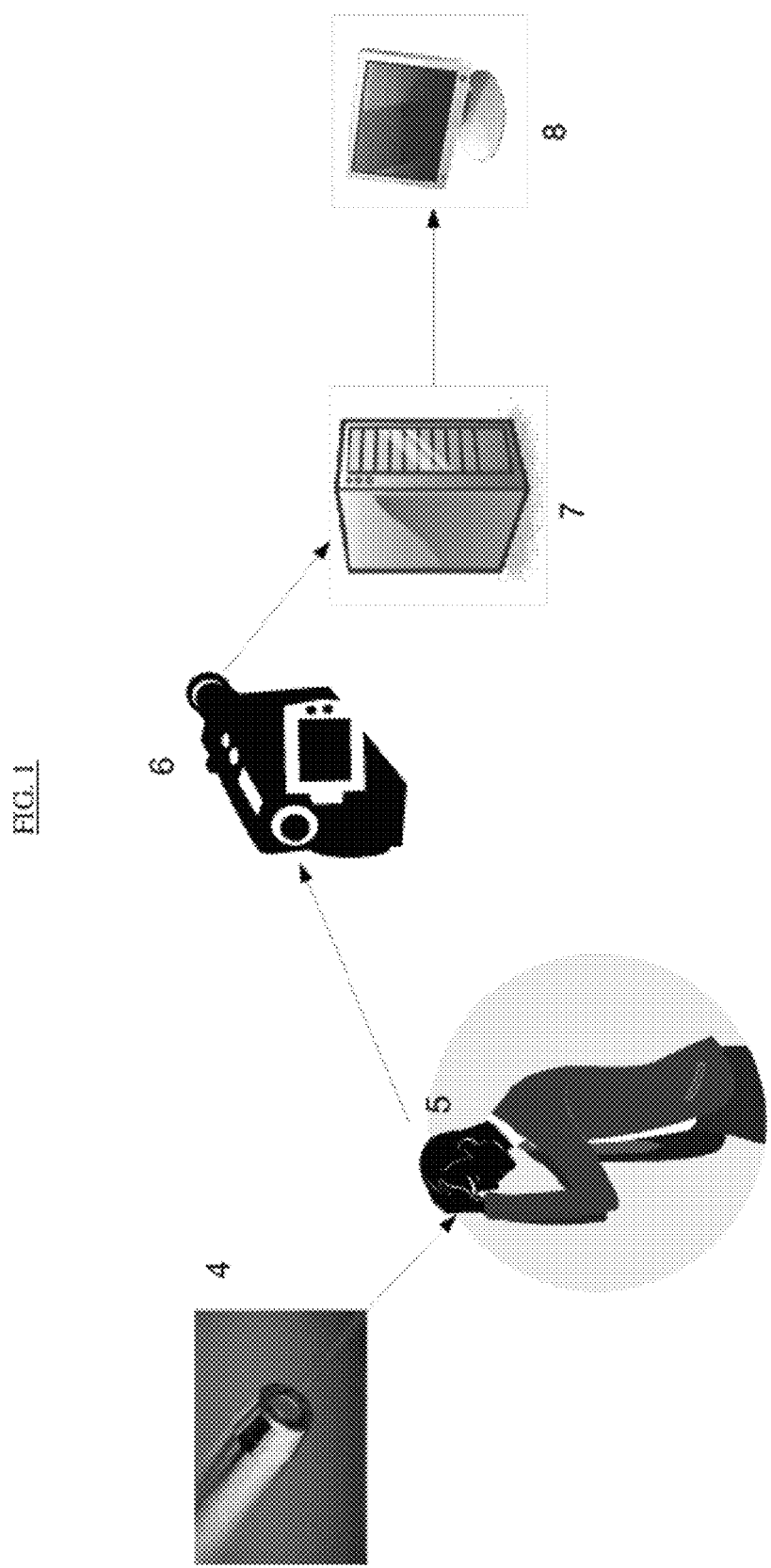
FIG. 1 schematically illustrates block diagram of the device for the visualisation of the surface tumours through the analysis of the multispectral fluorescent image, FIG. 2 schematically illustrates block diagram of the device for the visualisation of the sub-surface tumours through the analysis of the multispectral fluorescent image, FIG. 3 schematically illustrates block diagram of the approach for unsupervised segmentation of the multispectral fluorescent image and obtaining spatial map of the surface and sub-surface tumours with a good visual contrast, FIGS. 4A and 4B schematically illustrate spectral similarity between the classes $s_1$ and $s_2$ in appropriate spatial visualisation, FIG. 5 schematically illustrates spectrally similar and spectrally different classes $s_1$ and $s_2$ in the wavelength region, FIG. 6 schematically illustrates spectrally similar and spectrally different classes $s_1$ and $s_2$ in appropriate coordinate systems, FIG. 7 schematically illustrates quality of the spatial map of the healthy tissue $s_1$ and tumour $s_2$ which are extracted by direct application of the ICA algorithms to two-spectral image 4A, FIG. 8 schematically illustrates quality of the spatial map of the healthy tissue $s_1$ and tumour $s_2$ which are extracted by application of the ICA algorithms on multispectral image obtained after nonlinear dimensionality expansion and linear transform that yields innovations representation, to two-spectral image 4A.

Schematic block diagram of the device for the visualisation of the surface tumours through segmentation of the multispectral fluorescent image 1 is shown in FIG. 1. The device consists of: light source 4 used to illuminate the surface tissue 5 with the purpose to induce fluorescence; multispectral camera 6 with the purpose to record fluorescent image of the illuminated surface tumour; computer 7 where algorithms for unsupervised segmentation of the multispectral fluorescent image are implemented; monitor 8 used to display the spatial map of the surface tumours.

Figure 2:
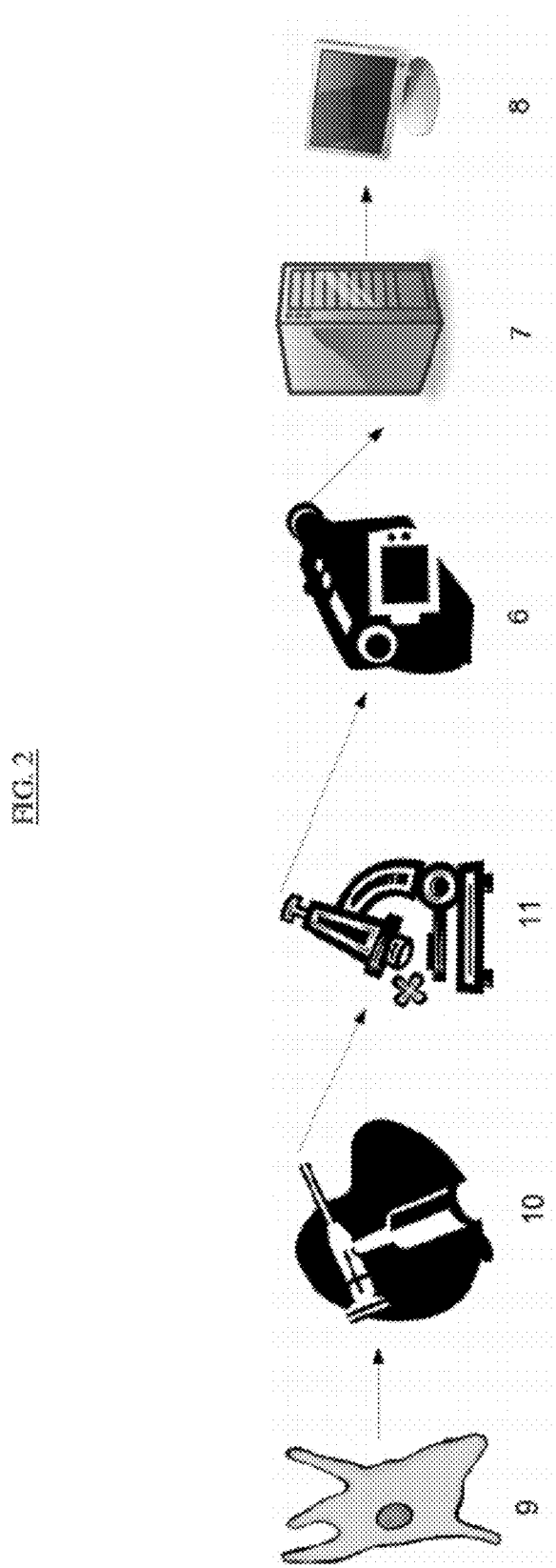

Schematic block diagram of the device for the visualisation of the sub-surface tumours through segmentation of the multispectral fluorescent image 1 is shown in FIG. 2. The device consists of: endoscope 10 used to illuminate tissue of interest 9 with the aim to induce fluorescence and transfer image to microscope 11; multispectral camera 6 used to record magnified image of the illuminated sub-surface tissue; computer 7 where algorithms for unsupervised segmentation of the multispectral fluorescent image are implemented; monitor 8 used to display the spatial map of the surface tumours.

Figure 3:
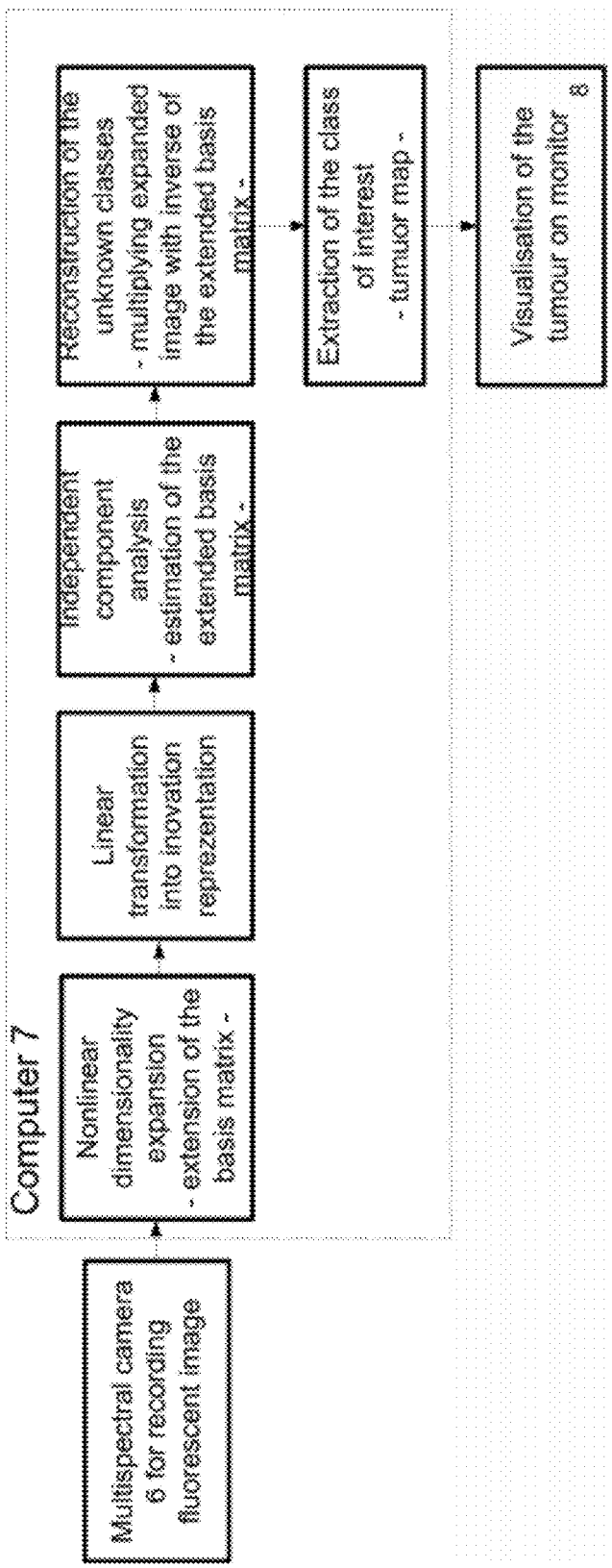

Procedure for processing multispectral fluorescent image with the aim to extract and visualise spatial map of the tumour with a good visual contrast is implemented in the software in the computer 7 and consists of the following steps schematically shown in FIG. 3: recorded multispectral image 1 is transformed by nonlinear dimensionality expansion transform into new multispectral image with the aim to increase spectral dissimilarity among the classes; multispectral image with increased dimensionality 2 is transformed by linear transform with the aim to increase statistical independence among the unknown classes yielding as a result innovations representation of the multispectral fluorescent image 3; independent component analysis algorithms are applied on innovations representation of the multispectral image in order to estimate extended basis matrix $\bar{A}$; as a final result the matrix of the unknown classes S is estimated. A spatial map of the tumour with enhanced visual contrast, which is extracted according to the chosen criteria and displayed on monitor 8, is among estimated matrix of the unknown classes S.

Procedure for real time visualisation and demarcation of the tumours using photodynamic method and segmentation of the fluorescent multispectral image consist of the following steps:

recording multispectral fluorescent image 1 with multispectral camera 6, where multispecral image is defined as a product of the unknown basis matrix A and matrix of the unknown classes S, transforming fluorescent multispectral image 1 into new multispectral image 2 by means of the nonlinear dimensionality expansion, where multispectral image 2 is defined as a product of the extended basis matrix $\bar{A}$ and matrix of the unknown classes S, linear transformation of the multispectral image 2 with extended dimensionality into innovations representation of the multispectral image 3 defined as a product of the extended basis matrix $\bar{A}$ and innovations representation of the matrix of the unknown classes $\tilde{S}$, estimation of the extended basis matrix $\bar{A}$ or its inverse $\bar{A}^{-1}$ by applying algorithms of the independent component analysis on innovations representation of the multispectral image (3), estimation of the matrix of unknown classes S through multiplication of the estimated inverse of the extended basis matrix $\bar{A}^{-1}$ and multispectral image 2, extraction of the spatial map of the tumour or class of interest in accordance with the chosen criteria, and displaying the tumour on monitor 8.

Problem of the unsupervised segmentation of the multispectral image I by means of the ICA algorithms can algebraically be expressed as a matrix factorization problem $X \in R_{0+}^{m \times N}$ by means of which multispectral image 1 is represented:

$$X = AS \quad [1]$$

In equation [1] X represents multispectral image 1 where $A \in R_{0+}^{m \times n}$ represents unknown basis matrix and $S \in R_{0+}^{n \times N}$ represents matrix of the unknown classes. In adopted notation m represents number of spectral components of the multispectral image, N represent number of pixels of the multispectral image, and n represents number of the unknown classes. Unsupervised segmentation methods estimate the unknown basis matrix A and unknown class matrix S using only the data matrix X and some a priori information about the classes. ICA algorithms assume that unknown classes are mutually statistically independent and non-Gaussian, as well as that number of linearly independent column vectors of the basis matrix is greater or equal to the number of unknown classes. These assumptions suffice to reconstruct the unknown classes by means of the ICA algorithms and multispectral image 1.

When multispectral image 1 is an RGB image the number of spectral components used in the representation described in the preceding paragraph is m=3. Number of unknown classes n contained in multispectral image 1 has to be estimated. One of the techniques used for this purpose is based on counting singular values of the data covariance matrix $R_{xx} = (1/N)XX^T$, that are greater than threshold value defined by the signal-to-noise ratio. If there exists some a priori knowledge about the image scene it is possible to set the number of the unknown classes n in advance. For example, if the image of the skin tumour is recorded it is logical to assume existence of the two classes in the image: tumour and healthy tissue. In such a case it follows n=2. Depending on the complexity of the scene this number can be increased. For example if the tumour on the head is imaged, the hair can also be one class in which case number of classes n should be set to 3.

In a case of the segmentation of the multispectral image 1 model defined by equation [1] has the following interpretation. Let m be number of spectral components. Let x be column vector m×1 in multispectral image 1 and let it represent pixel in the multispectral image. Element $x_i$ is intensity recorded on the ith wavelength. Basis matrix A contains n spectral responses of the unknown classes i.e. $A = [a_1 \, a_2 \ldots a_n]$. Let s be unknown column vector n×1 in the class matrix S, that is associated with A, and that has to be estimated. Then $s_i$ represents contribution of the class with spectral response $a_i$ in the pixel x. When A is known estimation of s is achieved by means of the least squares method. This is supervised segmentation. In the real world applications in medicine, agriculture and remote sensing it is difficult to know in advance spectral responses of the classes that are resident in the multispectral image 1. Thus, the case with the unknown basis matrix A is quite common in practice. When A is unknown the segmentation problem, i.e. estimation of s, becomes considerably more difficult and is known under the name of automated or unsupervised segmentation. When two classes are identical the corresponding column vectors of the unknown basis matrix A, which represent spectral responses of the appropriate classes, are parallel i.e. linearly dependent. Consequently, condition set in the preceding paragraph, number of linearly independent column vectors of the basis matrix is greater than or equal to the number of the unknown classes n, is not fulfilled. In addition to that, when the two classes are similar, for example tumour in the early phase of development is similar to the surrounding healthy tissue, corresponding column vectors of the unknown basis matrix A are almost parallel. Unsupervised segmentation of such multispectral images is a challenge for the algorithms and direct application of the ICA algorithms on multispectral image 1, in a case when it contains spectrally similar classes, does not produce an accurate result. Similar problem of the inaccurate segmentation also appears when the unknown number of classes n contained in the multispectral image is greater than the number of spectral components m in the multispectral image 1.

The purpose of the use of the algorithms for the nonlinear dimensionality expansion and blind separation of statistically dependent sources is that in combination with the ICA algorithms increase accuracy of the unsupervised segmentation of the multispectral image 1 when tumour and healthy tissue are spectrally similar. This can be expected in the early phase of tumour development or when the multispectral image is low-dimensional. FIGS. 4, 5 and 6 schematically illustrate effect of the mentioned algorithms in the segmentation of the spectrally similar classes.

According to the references cited in the preceding paragraphs, algorithm for nonlinear dimensionality expansion of the multispectral image can be described in the following way. Idea upon which algorithm for nonlinear dimensionality expansion is built follows from the assumption that the second order stochastic process is characterized by the statistics of the first and second order. When spectral images $x_i$, i=1, ... m, that represent row vectors of the multispectral image 1, are interpreted as the first order statistics it is then possible to generate the spectral images of the second order. They encompass linear and nonlinear correlations and cross-correlations contained in the multispectral image 1. Let $$\{x_i\}_{i=1}^{m}$$

be the set of the first order spectral images. First set of the spectral images of the second order is possible to obtain on the basis of autocorrelations. They are constructed multiplying each spectral image by itself $$\{x_i^2\}_{i=1}^{m}.$$

Second set of the spectral images of the second order is constructed on the basis of cross-correlations between all spectral images of the first order $$\{x_i x_j\}_{i,j=1, i \neq j}^{m}.$$

In overall this yields $$2m + \binom{m}{2}$$

of the spectral images. For example if the multispectral image 1 is an RGB image with m=3 then described method of nonlinear dimensionality expansion transforms RGB image into new multisepctral image with m=9 spectral bands. In this new higher-dimensional space classes that in original RGB resolution were similar become less similar. Let us denote multispectral image with expanded dimensionality 2 as $\overline{X}$. According to definition it is a product of the extended basis matrix $\overline{A}$ and matrix of the unknown classes S $$\overline{X} = \overline{A}S \qquad [2]$$

According to the explanation given in the preceding paragraphs, corresponding column vectors of the extended basis matrix $\overline{A}$ become less collinear i.e. number of linearly independent column vectors of the extended basis matrix $\overline{A}$ is greater than number of linearly independent column vectors of the basis matrix A. Thus, one of the basic conditions for successful application of the ICA algorithms to unsupervised segmentation of the multispectral image is fulfilled. If the dimensionality of the multispectral image 1 has to be increased further another set of the nonlinearly correlated spectral images can be generated as $$\{\sqrt{x_i}\}_{i=1}^{m}.$$

As explained in the existing state-of-the-art in the preceding paragraphs, ICA algorithms assume that unknown classes are mutually statistically independent and non-Gaussian. In many practical situations, for example in a case of biomedical signals, these assumptions are not completely true. One of them is the assumption about statistical independence between the classes. Important references that cover problem of the unsupervised segmentation of the statistically dependent classes are cited in the preceding paragraphs. The challenge is to find a linear operator T with the property $$T[\overline{X}] = T[\overline{A}S] = \overline{A}T[S] \qquad [3]$$

such that transformed classes T[S] are more statistically independent than classes S. The unknown expanded basis matrix $\overline{A}$ is estimated by applying ICA algorithms to the linearly transformed multispectral image 3. Some of the methods used to implement the linear operator T are fixed and adaptive filter banks. Alternative to the filter banks is the use of innovations representation of the multispectral image 2 and that is proposed in the invention. Use of innovations representation as a linear transform T in order to enhance accuracy of the standard ICA algorithms has been suggested for the first time in: Hyvärinen, A. Independent component analysis for time-dependent stochastic processes. Proc. Int. Conf. on Artificial Neural Networks ICANN'98, 541-546, Skovde, Sweden, 1998. Important property of the innovations representations T[S] is that they are always more statistically independent and more non-Gaussian than classes S. These are the two fundamental conditions that have to be fulfilled for the ICA algorithms in order to yield accurate results when applied to segmentation of the multispectral image. Linear transform T[S] used to realize innovations representation T of the unknown classes $s_i$, i=1, ..., n is $$\tilde{s}_i(t) = s_i(t) - E[s_i(t)|t, s_i(t-1)] \qquad [4]$$

where $s_i$ denotes ith row of the class matrix S, and E denotes operator of the mathematical expectations. When both sides in equation 4 are multiplied by unknown extended basis matrix $\overline{A}$ it is obtained $$\tilde{X} = \overline{A}\tilde{S} \qquad [5]$$

where in the comparison with equation 3 operator T has been substituted by notation '~', i.e.

$$T[\overline{X}] = \tilde{X} \text{ and } T[S] = \tilde{S}.$$

Innovations representation of the multispectral image 3 is in practice realized though application of the prediction-error filter on multispectral image 2. Prediction-error filter is estimated by means of the Levinson algorithm. Details can be found in: S. J. Orfanidis. Optimum Signal Processing—An Introduction, $2^{nd}$ ed. MacMillan Publishing Comp., New York, 1988.

When in accordance with FIG. 3 and the preceding paragraphs, multispectral image 1 has been transformed into multispectral image 3, the ICA algorithms are applied to multispectral image 3 in order to estimate the extended basis matrix $\overline{A}$ or its inverse $\overline{A}^{-1}$. The ICA algorithms perform this estimation in a way to minimize a functional $$F(\overline{A}^{-1}\tilde{\overline{X}}, \overline{A})$$

that represents measure of statistical independence among the non-Gaussian processes $$\tilde{S} = \overline{A}^{-1}\tilde{\overline{X}}.$$

More details about the techniques for construction of the functional F and associated ICA algorithms can be found in the references cited in the existing state-of-the-art in the preceding paragraphs. Multispectral image 2 is multiplied by estimated inverse of the extended basis matrix $\overline{A}^{-1}$ in order to estimate the unknown class matrix $S=\overline{A}^{-1}\overline{X}$. For a final selection of the class of interest from the unknown class matrix S additional criteria are used such as predictability, smoothness or sparseness. This depends on the a priori knowledge of the dimensions of the class of interest relative to the dimensions of the multispectral image (1).

Figure 4B:
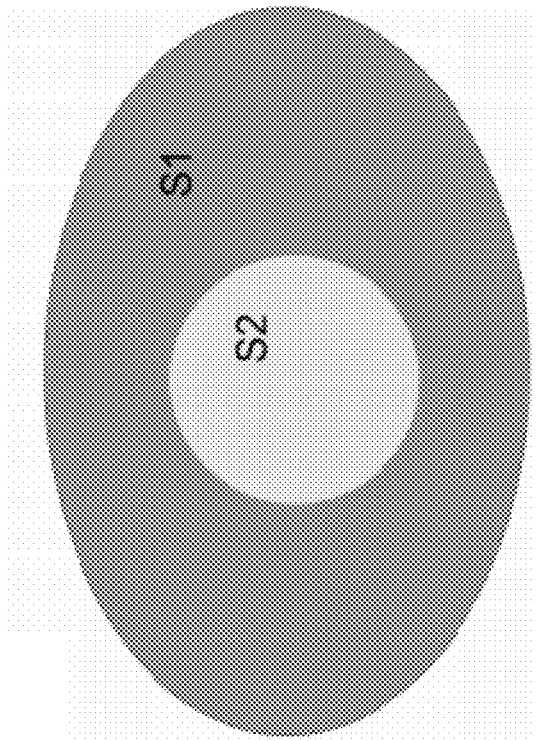
Figure 4A:
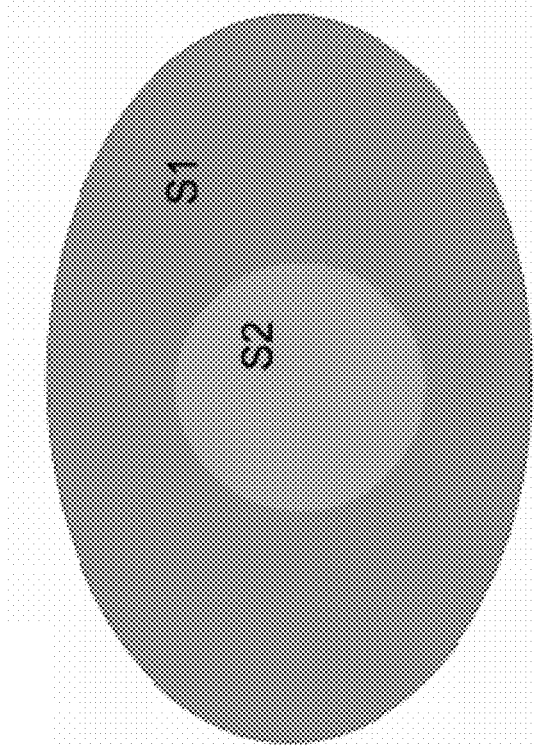
Figure 5:
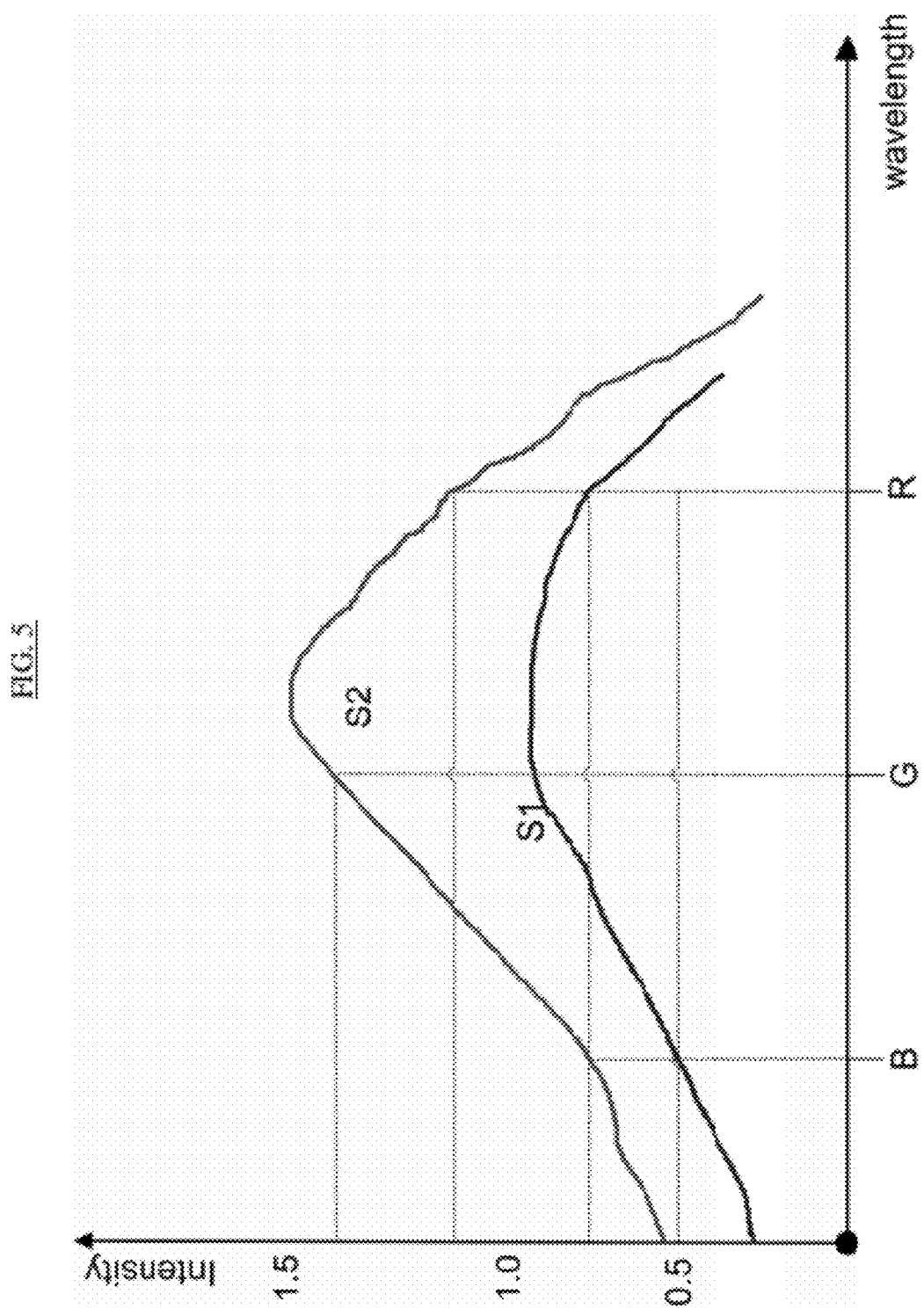

FIGS. 4A and 4B schematically illustrate the case of spectrally similar and spectrally different classes $s_1$ and $s_2$ in the appropriate spatial visualisation. FIG. 4A: classes $s_1$ and $s_2$ are spectrally very similar. FIG. 4B: classes $s_1$ and $s_2$ are spectrally different. By convention we shall assume that class $s_1$ represents healthy tissue, and class $s_2$ represents tumour.

FIG. 5 schematically illustrates the case of spectrally similar and spectrally different classes $s_1$ and $s_2$ in the wavelength region. Shown are spectral responses of the pixels located in the regions of classes $s_1$ and $s_2$ according to FIG. 4. In the adopted designation system B denotes spectral component that corresponds with the blue colour, G denotes spectral component that corresponds with the green colour, and R denotes spectral component that correspond with the red colour. In two-spectral resolution B-R classes $s_1$ and $s_2$ are spectrally very similar or even identical what corresponds with a FIG. 4A. In three-spectral resolution B-G-R classes $s_1$ and $s_2$ are spectrally different what corresponds with a FIG. 4B. Equivalence of the three-spectral B-G-R resolution can be obtained by application of the transformation for nonlinear dimensionality expansion and innovations representation to B-R image in two-spectral resolution. This yields effect shown in FIG. 4B.

FIG. 6 schematically illustrates the case of spectrally similar and spectrally different classes $S_i$ and $s_2$ in the appropriate coordinate systems. FIG. 6A: two-spectral resolution, two-dimensional B-R system, spectral vectors of the classes $s_1$ and $s_2$ are collinear. FIG. 6B: three-spectral resolution, three-dimensional B-G-R system, spectral vectors of the classes $s_1$ and $s_2$ are spread. Equivalence of the three-spectral B-G-R resolution can be obtained by application of the transforms for nonlinear dimensionality expansion and innovations representation to an image in two-spectral B-R resolution. This yields an effect illustrated in FIG. 4B.

Figure 7B:
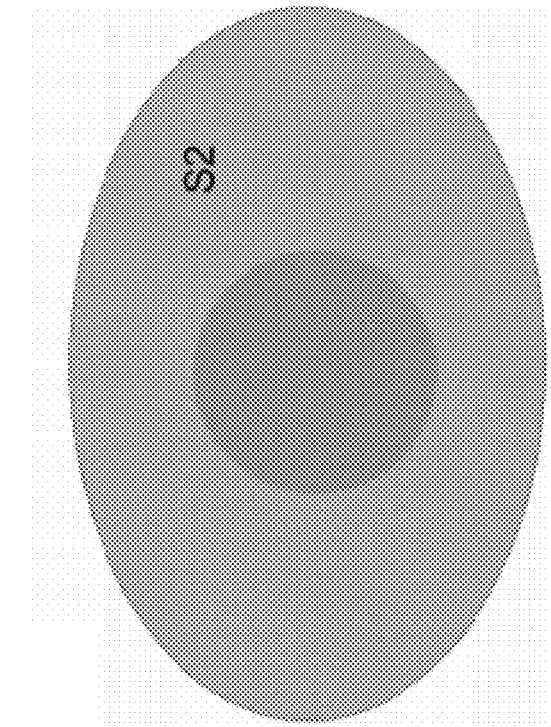
Figure 7A:
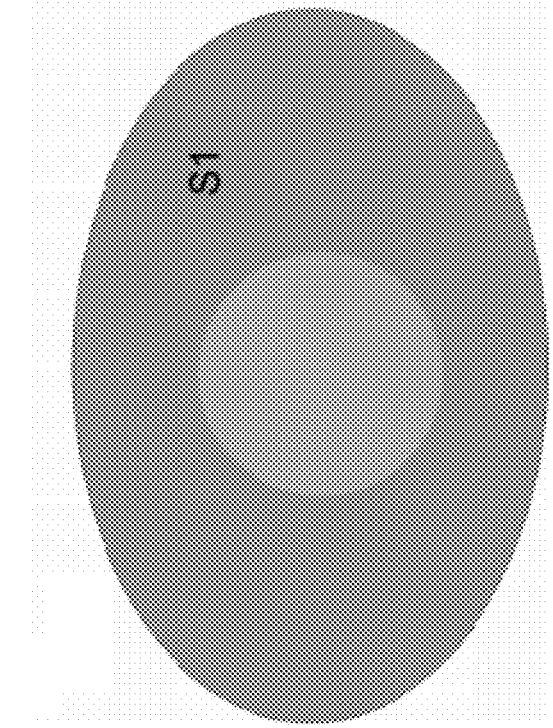

FIG. 7 schematically illustrates quality of the visual contrast of the spatial maps of the healthy tissue $s_1$ and tumour $s_2$ extracted by direct application of the ICA algorithms to multispectral image 1, as an example two-spectral image 4A. By convention black colour means class existence while white colour means class absence. FIG. 7A: extracted spatial map of the healthy tissue. FIG. 7B: extracted spatial map of the tumour. Visual contrast of the extracted spatial maps is poor.

FIG. 8 schematically illustrates quality of the visual contrast of the spatial maps of the healthy tissue $s_1$ and tumour $s_2$ extracted by applications of the ICA algorithms to the innovations representation of the multispectral image 3. Multispectral image 3 is obtained by application of the nonlinear dimensionality expansion transform and linear innovations representation transformation to multispectral image 1, as an example two-spectral image 4A. By convention black colour means class existence while white colour means class absence. FIG. 8A shows extracted spatial map of the healthy tissue. FIG. 8B shows extracted spatial map of the tumour. Visual contrast of the extracted spatial maps is good.

Figure 9B:
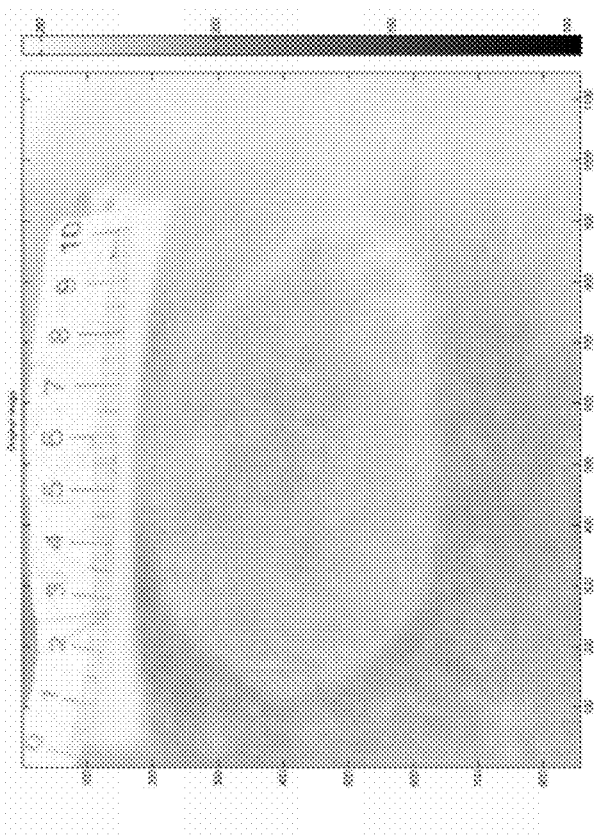
FIGS. 9A and 9B respectively show tumour with the high level of the fluorescence and the same tumour with the low level of the fluorescence.
Figure 9A:
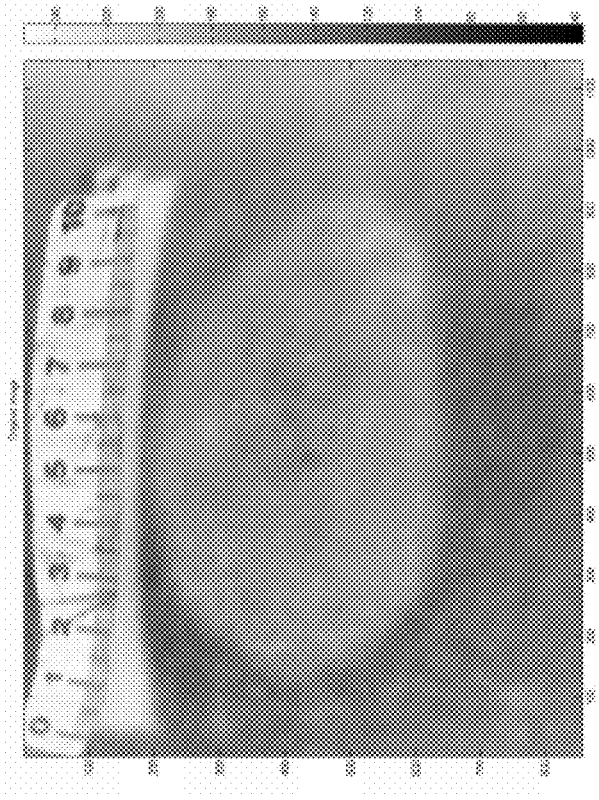

FIGS. 9A and 9B respectively show skin tumour with the high level and low level of fluorescence. As it is evident in FIG. 9B the demarcation line of the tumour is hardly visible i.e. the visual contrast is very poor.

Figure 10B:
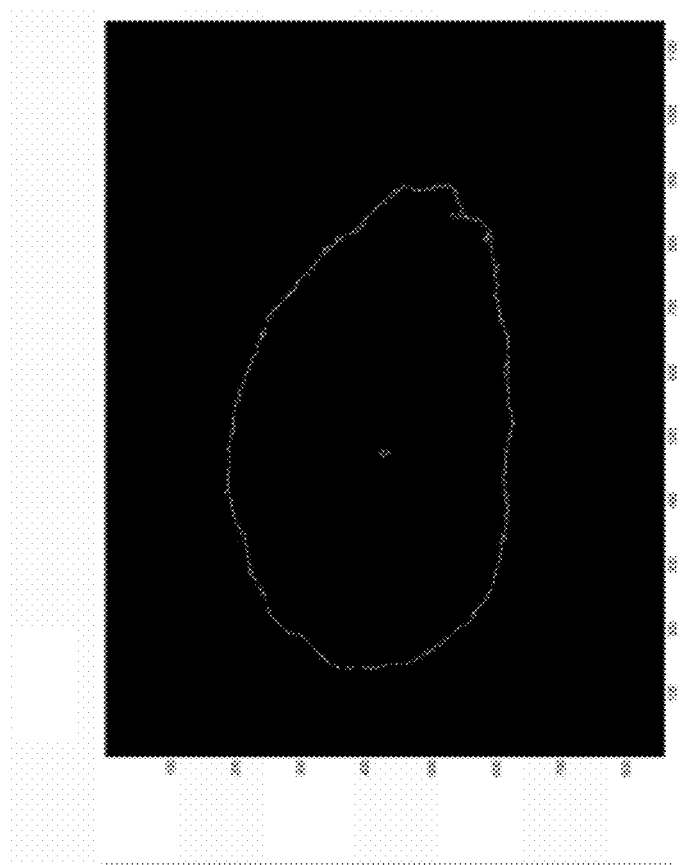
FIGS. 10A and 10B respectively show demarcation lines of the tumours shown on FIGS. 9A and 9B, which are obtained by described invention that combines nonlinear dimensionality expansion, innovations representations and independent component analysis, FIGS. 11A and 11B respectively show demarcation lines of the tumours shown on FIGS. 9A and 9B, which are extracted by the ratio imaging method with a threshold value set to 5 in accordance to the existing state-of-the-art, and FIGS. 12A and 12B respectively show demarcation lines of the tumours shown in FIGS. 9A and 9B, which are extracted by the ratio imaging method with a threshold value set to 10 in accordance with the existing state-of-the-art.
Figure 10A:
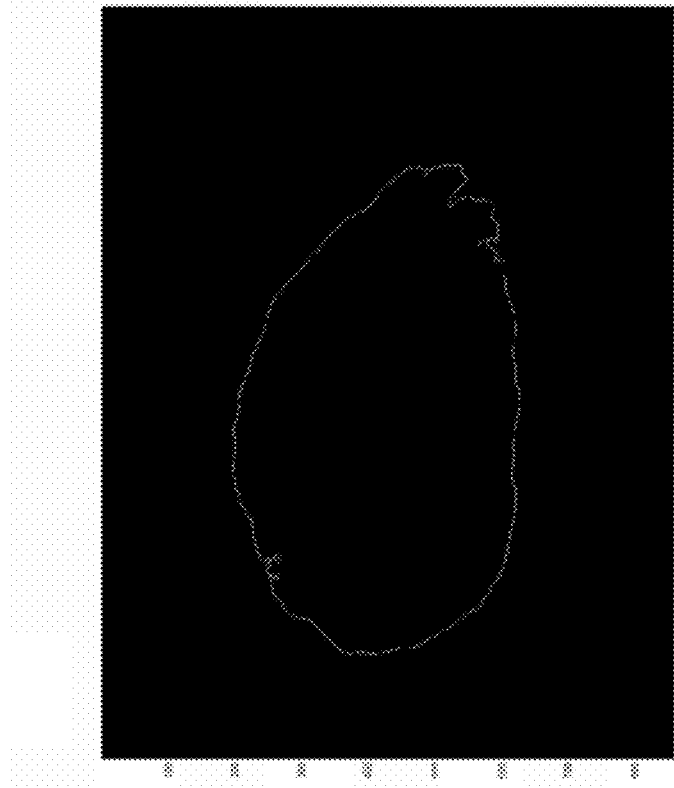

FIGS. 10A and 10B respectively show demarcation line of the tumour extracted by the proposed invention. FIG. 10A is obtained by application of the invention to FIG. 9A. FIG. 10B is obtained by application of the invention to FIG. 9B. It is evident that proposed invention extracts, approximately, the same demarcation line in both cases. This demonstrates its robustness with respect to the variability of intensity level of the fluorescent image.

Figure 11B:
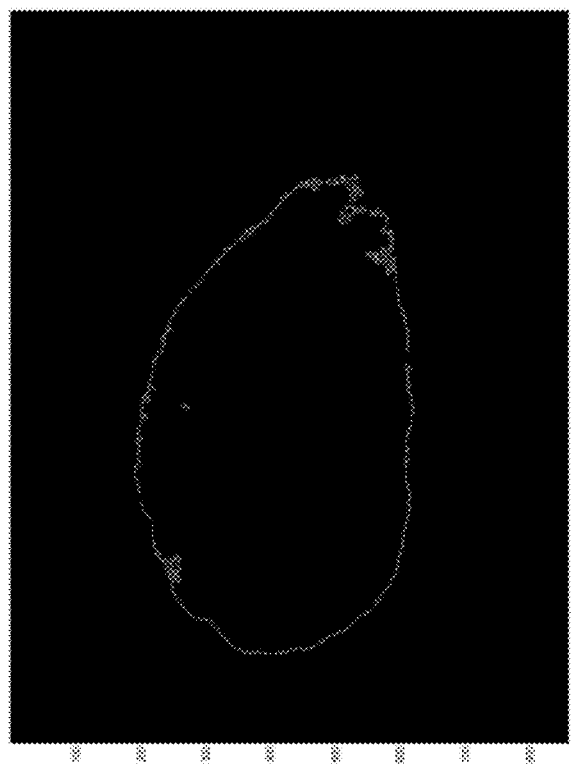
Figure 11A:
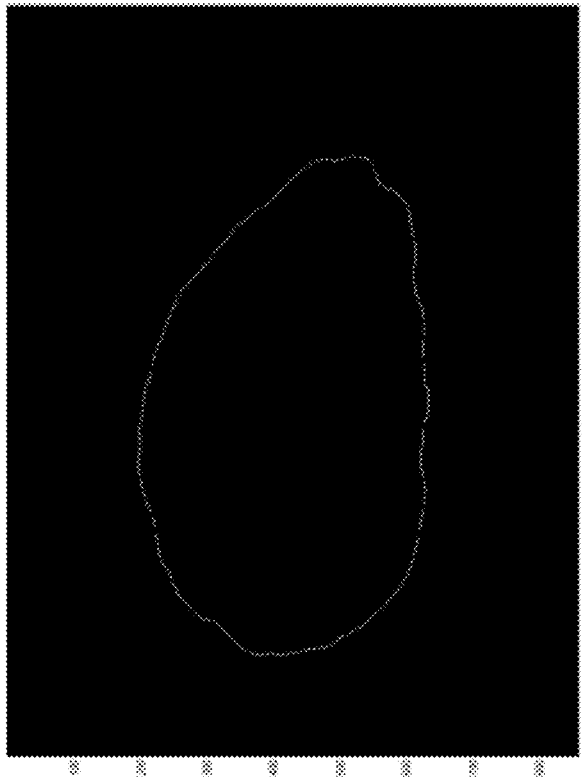

FIGS. 11A and 11B respectively show demarcation line of the tumour extracted by the ratio imaging method according to the existing state-of-the-art, from FIGS. 9A and 9B. The threshold value was 5. Small effects of the variation of the intensity level of the fluorescence are visible in FIG. 11B.

Figure 12B:
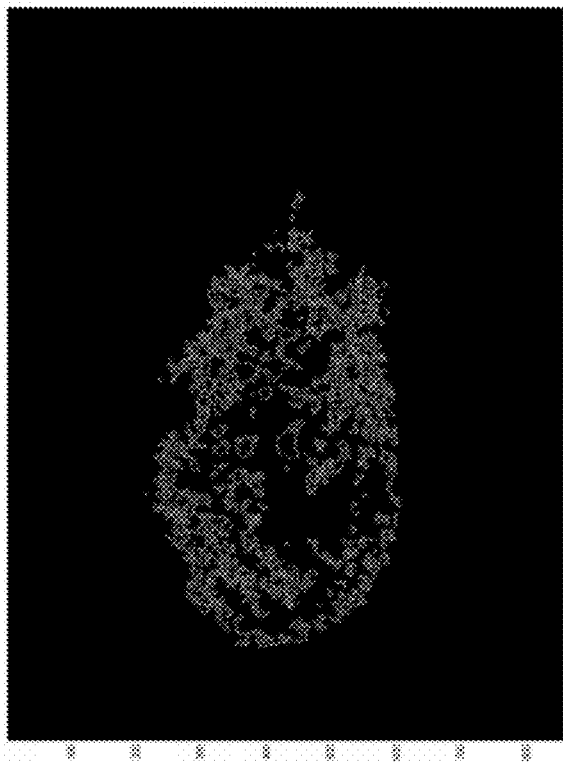
Figure 12A:
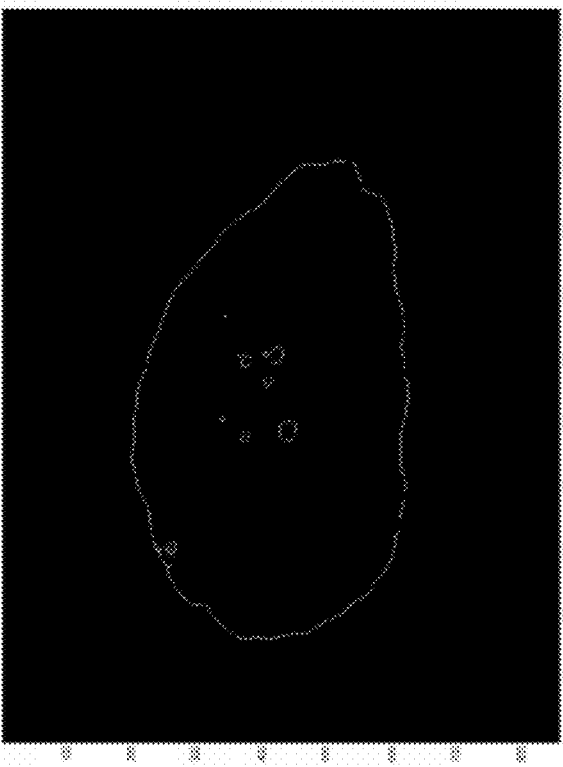

FIGS. 12A and 12B respectively show demarcation line of the tumour extracted by the ratio imaging method according to the existing state-of-the-art, from FIGS. 9A and 9B. The threshold value was 10. Effects of the variation of the intensity level of the fluorescence are clearly visible on FIG. 12B when threshold value has been set to 10. Since the optimal value of the threshold depends on the intensity of the illuminating light, concentration level of the photo sensitizer and time duration of the treatment of the tumour by means of the photo sensitizer, it is clear that the ratio imaging is very sensitive on the variability of these parameters.

Invention can also be applied to suppress reflected illumination in the multiple fluorescence based photodynamic therapy systems. It is characteristic for such systems that fluorescence induced by one illumination is superimposed with reflections of another illumination. Because radiations spectrally overlap, it can be expected that they are statistically partially dependent. By application of the proposed invention it is possible to achieve higher suppression level of the reflected radiation than when ICA algorithms are directly used for the same purpose.

Proposed invention can be additionally applied during tumour surgery by estimating tumour boundaries in real time. This eliminates necessity to perform a biopsy on the tissue sample and to wait for the outcome during the surgery in order to assess the tumour boundaries. The invention can also be applied to segmentation of the multispectral fluorescent image of the tissue 1 acquired when the time interval of the treatment of the tumour with the photo sensitizer is shortened or when the concentration of the photo sensitizer is reduced. Proposed invention is applied to unsupervised segmentation of the multispectral fluorescent image 1 acquired under reduced intensity of the illuminating light, that becomes especially important for the surgery of the brain tumour and for the monitoring of the therapy.

The invention claimed is:
1. A method for visualizing and demarcating tumors by performing photodynamic methods and analysis of a multispectral fluorescent image, the method comprising:
recording a first multispectral image with a multispectral camera, the first multispectral image being represented by a linear mixture model defined by the equation:

$$X=AS$$

wherein A is an unknown matrix of spectral profiles, and S is an unknown matrix of spatial maps of classes present in the first multispectral image, wherein the classes present in the first multispectral image comprise a first class corresponding to a tumor or unhealthy tissue, a second class corresponding to healthy tissue, and a third class corresponding to other tissue types present in the first multispectral image;
transforming the first multispectral image into a second multispectral image with extended dimensionality by using nonlinear dimensionality expansion, the second multispectral image being represented by the equation:

$$\overline{X}=\overline{A}S$$

wherein $\overline{A}$ is an unknown matrix of spectral profiles with extended dimensionality;
linearly transforming the second multispectral image into a first innovation representation of the second multispectral image according to the equation:

$$T[\overline{X}]=\overline{A}T[S]$$

wherein T[S] is a second innovation representation of the matrix S;
performing independent component analysis on the first innovation representation to estimate at least one of the unknown matrix of spectral profiles with extended dimensionality, $\overline{A}$, and its inverse, $\overline{A}^{-1}$;
estimating the unknown matrix of spatial maps of classes present in the first multispectral image S by multiplying the second multispectral image $\overline{X}$ by $\overline{A}^{-1}$;
extracting data of interest comprising at least one of a tumor map, the first class, the second class and the third class according to selected criteria; and
visualizing the tumor.

2. The method of claim 1, further comprising:
generating spectral components $x_i$ of a second order from the first multispectral image,
wherein the spectral components $x_i$ of the second order encompass linear and nonlinear correlations and cross-correlations comprised in the first multispectral image.

3. The method of claim 2, wherein the step of generating spectral components of the second order from the first multispectral image comprises:
calculating a second power of the spectral components $x_i$ of the first multispectral image; and
mutually multiplying spectral components $x_i x_j$ of the first multispectral image.

4. The method of claim 2, further comprising:
extending dimensionality of the second multispectral image by generating nonlinearly correlated spectral images,
wherein the nonlinearly correlated spectral images are generated by calculating the square root of the spectral components $x$, of the first multispectral image.

5. The method of claim 1, wherein the step of extracting at least one of a tumor map, the first class, the second class and the third class according to selected criteria is performed by reconstructing matrix S according to additional criteria based on a priori assumed spatial dimensions of the data of interest relative to spatial size of the first multispectral image,
wherein the additional criteria comprises at least one of predictability, smoothness and sparseness.

6. The method of claim 1, wherein the data of interest is at least one of a surface tumor and sub-surface tumor.

7. The method of claim 1, wherein the data of interest is any type of unhealthy tissue.

8. The method of claim 1, wherein the method is performed by means of unsupervised segmentation of the first multispectral image recorded with at least one of reduced concentration of photo sensitizer, reduced intensity of illuminating light and reduced duration of treatment by photo sensitizer.

9. The method of claim 8, wherein the method is performed during at least one of real-time estimation of tumor boundaries and monitoring of therapy.

* * * * *